(12) United States Patent
Chapman et al.

(10) Patent No.: US 10,791,731 B2
(45) Date of Patent: Oct. 6, 2020

(54) METHODS FOR PREPARING FROZEN PLASMA MATERIAL FOR RAPID THAWING IN AN EMERGENCY SITUATION

(71) Applicant: THE REGENTS OF THE UNIVERSITY OF COLORADO, a body corporate, Denver, CO (US)

(72) Inventors: Michael P. Chapman, Denver, CO (US); Ernest Moore, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/580,980

(22) PCT Filed: Jun. 8, 2016

(86) PCT No.: PCT/US2016/036492
§ 371 (c)(1),
(2) Date: Dec. 8, 2017

(87) PCT Pub. No.: WO2016/200980
PCT Pub. Date: Dec. 15, 2016

(65) Prior Publication Data
US 2018/0177180 A1     Jun. 28, 2018

Related U.S. Application Data

(60) Provisional application No. 62/172,667, filed on Jun. 8, 2015.

(51) Int. Cl.
*A01N 1/02* (2006.01)
*A61M 1/02* (2006.01)
*A61K 35/16* (2015.01)

(52) U.S. Cl.
CPC .......... *A01N 1/0263* (2013.01); *A01N 1/0273* (2013.01); *A01N 1/0284* (2013.01); *A61K 35/16* (2013.01); *A61M 1/025* (2013.01); *A61M 1/0277* (2014.02); *A61M 1/0281* (2013.01); *A61M 2205/3368* (2013.01); *A61M 2205/366* (2013.01)

(58) Field of Classification Search
None
See application file for complete search history.

(56) References Cited

U.S. PATENT DOCUMENTS

| | | | |
|---|---|---|---|
| 4,117,881 A | 10/1978 | Williams et al. | |
| 4,565,073 A * | 1/1986 | Lavender | A01N 1/02 206/425 |
| 5,863,715 A | 1/1999 | Rajotte et al. | |
| 6,748,164 B1 | 6/2004 | Kuzyk | |
| D645,975 S | 9/2011 | Barkey | |
| 2003/0075516 A1 | 4/2003 | Rothman et al. | |
| 2004/0110289 A1* | 6/2004 | Ludlow | C12N 5/067 435/370 |
| 2006/0070392 A1* | 4/2006 | Heuser | A01N 1/00 62/373 |
| 2007/0028642 A1 | 2/2007 | Glade et al. | |
| 2010/0072216 A1 | 3/2010 | Voute et al. | |
| 2010/0281886 A1 | 11/2010 | Shaham et al. | |
| 2014/0255909 A1 | 9/2014 | Walter et al. | |

FOREIGN PATENT DOCUMENTS

WO    2013053011 A1    4/2013

OTHER PUBLICATIONS

Rackyard.com: Blood Bags, Blood Bags Storage Canisters, 2012, retrieved from the internet Apr. 11, 2019: http://www.rackyard.com/medial/blood-bag.html.*
Hardwick et al., Section 12, Blood storage and transportation, Introduction to Blood Transfusion Technology, ISBT Science Series (2008) vol. 3, pp. 177-196.*
International Preliminary Report on Patentability for International (PCT) Patent Application No. PCT/US2016/036492 dated Dec. 21, 2017, 10 pages.
International Search Report for International Patent Application No. PCT/US2016/036492, dated Sep. 13, 2016, 3 pages.
Written Opinion for International Patent Application No. PCT/US2016/036492, dated Sep. 13, 2016, 8 pages.
EPO, "Extended European Search Report", Application No. 16808210.5, dated May 2, 2019, 11 pages.
Podlasek, Stanley J. et al., "Rapid thawing of Fresh Frozen Plasma in Two-Liter Bags", American Journal of Emergency Medicine vol. 8, No. 6, Nov. 1990, pp. 475-478.

* cited by examiner

*Primary Examiner* — Scott Long
*Assistant Examiner* — Evelyn Y Pyla
(74) *Attorney, Agent, or Firm* — Dorsey & Whitney LLP

(57) ABSTRACT

Systems for controlled freezing, storing and thawing a biological material in a bag and supporting apparatus. The systems are adapted to receive the biological material therein for freezing, storing, transporting and rapid thawing immediately prior to administration to a patient in need of the biological material.

20 Claims, 3 Drawing Sheets

METHODS FOR PREPARING FROZEN PLASMA MATERIAL FOR RAPID THAWING IN AN EMERGENCY SITUATION

CROSS REFERENCE TO RELATED APPLICATIONS

This application is a national stage application under 35 U.S.C. 371 of PCT Application No. PCT/US2016/036492 having an international filing date of Jun. 8, 2016, which designated the United States, which PCT application claimed the benefit of U.S. Application Ser. No. 62/172,667, filed Jun. 8, 2015, both of which are herein incorporated by reference in their entirety.

GOVERNMENT INTEREST

This invention was made with Government support under grant number W81XWH1220028 awarded by the US Army Medical Research Acquisition Act of the Department of Defense. The U.S. Government has certain rights in the invention.

TECHNICAL FIELD

The invention relates to systems and methods for transporting, freezing, storing, and thawing of biological materials, particularly such systems for emergent use in traumatic and non-traumatic hemorrhage circumstances.

BACKGROUND OF DISCLOSURE

Storing frozen biological material, such as blood plasma, and then thawing it for transfusions is a common practice at health care facilities. For example, bags of plasma are typically frozen to preserve the plasma for subsequent use. For this purpose, plasma is usually stored frozen in a sealed prepackaged bag. Before the frozen bag of plasma can be used for a transfusion, the frozen plasma must first be heated to a desired transfusable temperature. Conventionally, a wet bath has been used to thaw and warm the frozen plasma. To accomplish this thawing and warming, a bag of the frozen plasma is placed directly into a liquid bath which has been preheated to a temperature necessary to thaw the frozen plasma. One of the problems associated with using a wet bath to effect plasma thawing is that contamination of the entire bath will occur if the plasma bag inadvertently leaks or breaks during the thawing process. Additionally, contaminants in the bath may be transferred to the bag of plasma. Consequently, as an alternative to thawing the plasma by direct insertion into a wet bath, an overwrap bag has also been used to cover and protect the bags of plasma, or other biological materials, and to isolate the bag in case of breakage. The disadvantage of overwrap bags is that they must also be sealed to prevent leakage, and they become wet on the outside and must be wiped off with a towel. As a result, the towel and the overwrap bag become a potential breeding ground for bacteria, and care must be taken to avoid the contamination of the plasma bag by the towel and overwrap bag itself.

As another matter, it is often desirable to thaw biological material rapidly, particularly in emergency situations. Rapid thawing of biological materials limits the amount of time thawed material sits in storage and reduces waste produced when plasma bags are thawed slowly in advance of an emergency use situation that does not materialize, requiring the thawed plasma to be discarded. Thawed plasma has a limited shelf life, and coagulant factors in thawed plasma can degrade in a relatively short period of time. If thawing time is relatively long, medical professionals will often compensate by removing extra frozen units of plasma out of cold storage in advance of an emergency operation, so that a large volume of thawed plasma can be available by the time of its anticipated use. This results in wasted plasma if some of the extra units are not needed for the operation or transfusion. Thus, rapid thawing allows medical professionals to have the proper amount of frozen biological materials on an as-needed basis, thereby reducing the potential for wasted materials. Accordingly, a system including apparatus and methods for quickly thawing frozen biological materials is desired, particularly to allow delivery of freshly thawed, frozen AB (universal donor) plasma to trauma victims at the scene of injury. This disclosure provides such system and components meeting these needs and having additional advantages.

These aspects of the disclosure are pointed out with particularity in the appended claims. To gain an improved understanding of the advantages and features, reference may be made to the following descriptive matter and accompanying figures that describe and illustrate various configurations and concepts related to the disclosure.

SUMMARY OF INVENTION

An aspect of this disclosure provides a flexible bag for receiving and housing a biological material. The bag is preferably made of a polymeric material that is able to conduct heat and may be sterile and/or disposable and is able to withstand damage such as shock, abrasion, impact, or other mishandling events that may be encountered in freezing, thawing, or transportation of these containers before and after addition of a biological material. Thus, this aspect of this disclosure provides a container for freezing, storing and thawing a biological material. The container comprises a polymeric material suitable to receive the biological material for freezing, storing and thawing in liquid or frozen state, and the container includes at least one port to introduce and/or evacuate the biological material in the bag. The bag may be an ultra-high surface area (UHSA) flexible bag for freezing, storing and thawing frozen plasma. Such UHSA may include, but is not limited to, flat, tubular, coiled, folded or perforated plasma packaging systems.

In a second aspect, the present invention provides a support container for freezing, storing and transporting the bag of biological material which includes a foldable or hinged exterior shell capable of receiving, storing and protecting the bag of biological material therein.

In a third aspect, the present invention provides a method for freezing, storing and thawing a biological material. The method includes providing a support container adapted to contain the bag of biological material for freezing, storing and thawing, and positioning the bag in the support container for supporting and protecting the bag. The support container containing the bag is then subjected to freezing temperatures thereby freezing the bag in the support container. At a time when the bag of biological materials is desired to be thawed, the support container containing the bag is removed from the freezing temperatures and the bag is removed from the support container and thawed.

In a fourth aspect, the present invention provides a transport crate adapted to storing and transporting the bag of biological material in the container. The transport crate is formed in a size and shape for receiving at least one support container containing the bag of biological material and securing the at least one support container for protection during transport, especially transportation during emergency situations. The transport crate also provides thermal protection sufficient to maintain the frozen state of the biological material in the bag in the support container for at least eight hours.

In a fifth aspect, the present invention provides a temperature control unit adapted to rapidly thaw the bag of biological material. The temperature control unit provides a heating (i.e., thawing) methodology specifically engineered for compatibility with the bag. The heating methodology includes, but is not limited to, convective liquid heat transfer, conformal/flexible conductive contact heating systems, radiant heating systems, inductive heating systems and microwave or other low frequency electromagnetic radiant based systems, as well as associated mechanical agitation methodologies.

The temperature control unit may include a first surface and a second surface facing the first surface. The temperature control unit is configured to receive the bag of frozen biological material and the bag substantially conforms to the shape of the first and second surfaces such that the bag contacts the first surface and the second surface of the temperature control unit. The first and/or second surfaces of the temperature control unit include a heat transfer surface that may be heated to thaw the frozen biological material in the bag and/or heat and/or maintain the temperature of the biological material in the bag disposed in the temperature control unit. The first and/or second surfaces of the temperature control unit may comprise a bladder that can be filled with a fluid that may be heated to a desired temperature and pumped into the bladder to expand the bladder wall against the bag of biological material, thereby heating and/or agitating the biological material. The heated fluid is maintained in the bladder to transfer heat through the bladder wall to the bag. Fluid may then be withdrawn from the bladder to retract the bladder wall away from the bag.

Another aspect of this disclosure provides a method for thawing and heating biological materials in a bag. The bag is placed in contact with the first surface and the second surface of the temperature control unit and the first and/or second surfaces are heated to the desired temperature to thaw the biological material in the bag. The bag of thawed and/or heated biological material is then removed from contact with the first and second surfaces of the temperature control unit.

Another aspect of this disclosure provides a system for freezing, storing and thawing a biological material which includes a flexible bag, a support container, a transport crate, and a temperature control unit. The flexible bag is adapted to receive a liquid biological material therein for freezing, storing and thawing, wherein the bag fully encloses the biological material. The support container is configured to receive and protect the bag containing a biological material for freezing, storing and transporting. The transport crate is configured to receive at least one support container to protect and substantially maintain the temperature of the biological material in the bag in the support container in the transport crate. The temperature control unit includes a first surface and a second surface facing the first surface configured to receive the bag between the first and second surfaces to transfer heat from the first and/or second surface(s) to thaw, heat, and/or maintain the temperature of the biological material in the bag, in the temperature control unit.

The biological material may be any biological material that can be thawed in a container using the thawing apparatuses described herein. In example embodiments, the biological material comprises cells, e.g., cryopreserved cells, which may include stem cells. In other example embodiments, the biological material comprises blood, e.g., human or animal blood, or blood components, e.g., plasma, fresh frozen plasma (FFP), plasma frozen within 24 hours after phlebotomy (FP24).

These systems and devices may be designed and configured for use in transporting frozen biological materials and thawing and delivering the biological materials in environments that may include ambulances, helicopters, battlefields, seagoing vessels, field hospitals, hospitals in remote locations and developing countries, or any location with minimal infrastructural support, but where injuries and other medical emergencies are likely to occur. Such designs may include, for example, ruggedization or other modifications to existing technologies to render them usable in the above-described environments.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become more readily apparent from the Description of Embodiments, particularly when taken together with the drawings.

DESCRIPTION OF EMBODIMENTS

Figure 1:
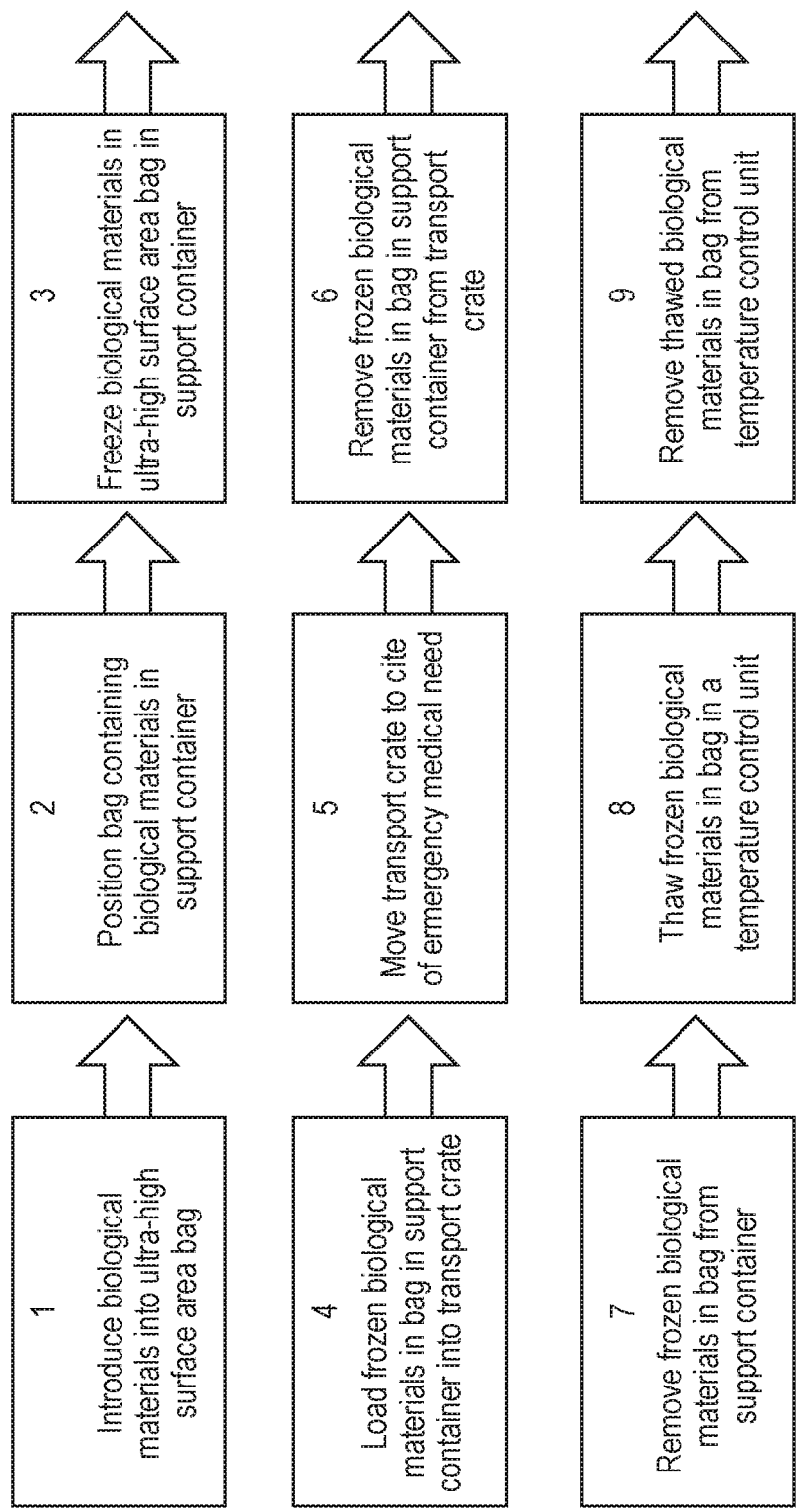
FIG. 1 shows a flow chart of methods and systems of freezing, storing, transporting and thawing biological materials.

The present disclosure is drawn to a system and apparatus that rapidly freezes, stores, protects, and thaws biological materials for safe and effective administration of these materials to humans in remote or emergency situations.

Currently, most trauma centers and emergency services use pre-thawed plasma to deliver plasma on demand at the scene of injury. While pre-thawed plasma presents some logistical advantages, there are significant disadvantages to its use. For example, pre-thawed, previously frozen plasma has a nominal shelf life of five days, but has been shown to degrade rapidly in terms of both its hemostatic and anti-inflammatory potential. Moreover, as the targeted patient population presents infrequently, a city wide fleet of ambulances would need to carry thawed plasma at all times, resulting in the waste of many thousands of units of AB plasma per year, lost to expiration. This would cost several million dollars per year for most mid-sized to large cities, and deplete these regions of a precious medical resource, as AB donors comprise less than 3% of the donor pool. This same fundamental problem of massive waste is encountered when keeping thawed universal donor plasma available for immediate emergency transfusion in ambulances, hospital emergency departments, and especially in remote locations or military applications where the supply chain is even more problematic. Additionally, lyophilized plasma and other room temperature stable products are not approved for use in the United States.

Delivery of freshly thawed, frozen AB (universal donor) plasma to trauma victims at the scene of injury was an unresolved technical challenge solved by the systems and apparatus of the present invention. The systems and methods provided herein can thaw plasma in three minutes or less, which should be compared to roughly 20 minutes for existing systems. This time differential represents an unacceptable delay in the delivery of emergency resuscitation fluids to traumatically injured or otherwise critically ill patients. Thus, the systems and methods of the present invention make the provision of emergency resuscitation fluids possible in circumstances when they are critically needed but currently unavailable, making the instant systems that store, transport, and rapidly thaw biological materials, such as plasma, in emergency situations, such as an ambulance fleet, a major improvement over existing technology.

The only other existing methodology for rapid plasma thawing is a microwave based system. This system has proven unacceptable on several counts. First, its thaw times are unpredictable ranging from four to eight minutes and occasionally far longer depending on the shape and volume of the plasma unit. The microwave is difficult to load and use, and mishandling during the stress of a trauma response can result in burned plasma, partially frozen plasma or punctured bags. The microwaves were also bulky and fragile and draw enormous amounts of electrical power, all of which render them largely unsuitable for installation in emergency vehicles. In short, these microwave systems are neither sufficiently robust nor fool proof to be used in a mobile/first response environment, and, above all, these microwave systems do not fail safe.

Thus, the present invention provides an entirely new methodology for rapid plasma thawing. Systems and apparatus for the freezing, safe transport, and rapid thawing of biological materials are depicted in FIG. 1, which provides a flow chart of one aspect of the present invention.

Referring to FIG. 1, biological materials, such as human plasma, are introduced into a sterile bag for storage (1). Any bag suitable for freezing biological material can be used in the systems and thawing apparatus described herein. Such bags may be made of any material known in the art, e.g., plastic, polystyrene, polyolefin, high density polyethylene, etc. Additionally, or alternatively, the bag may include a biocompatible layer on the interior surface of the bag, which layer may be formed of a low density polyethylene, very low density polyethylene ethylene vinyl acetate copolymer, polyester, polyamide, polyvinylchloride, polypropylene, polyfluoroethylene, polyvinylidenefluoride, polyurethane or fluoroethylenepropylene, for example. The bag is compatible with warm and cold conditions and may be able to withstand ionizing irradiation for sterilization purposes. The bag may be compatible with variations in temperature from 100 C to ultra-cold temperatures to −180° C. or even −200° C. or even colder, which temperature range includes the preferable freezing temperatures of 0° C., −18° C., −20° C., −25° C., −30° C., −40° C., −70° C., and −80° C., for example, and the preferable thawing temperatures of 23° C., 37° C., 42° C., 50° C., 60° C., and 100° C., for example. Preferably, the bag may have a large surface area to volume ratio, and a relatively thin wall thus promoting heat transfer therethrough when received in a temperature control unit, as described in detail below. Also, the bag may be disposable, thus promoting ease of use and preventing cross-contamination of the interior of the bag which might result when reusing other types of containers, etc.

The bag may have an interior volume ranging from 0.01-100 liters, for example. The containers may have a volume of 100 µl to 500 µl, 500 µl to 1 ml, 1 ml to 2 ml, 1 ml to 5 ml, 5 ml to 10 ml, 10 ml to 25 ml, 25 ml to 50 ml, 50 ml to 100 ml, 100 ml to 1 L, 1 L to 2 L, or 2 L to 5 L. In example embodiments, the containers may have a volume of about 2 L.

The bag may comprise ports and/or tubes to allow filling or draining of biological materials or other solids, liquids, or gases into and/or out of the interior of the bag. Such conduits may also be used to insert measurement probe(s) into the bag (e.g., a pH electrode, a conductivity sensor, temperature probe, an ion selective electrode, a spectophotometric probe, an ultrasound sensor, an optic fiber.) Such conduits may be positioned around any edge of the bag to facilitate filling and/or drainage of the bag. Such conduits may be integral to flexible container or connectable to a port using a fitting placed on the inlet port. Such conduits and/or ports maintain the sterility of the contents of the bag.

Figure 2:
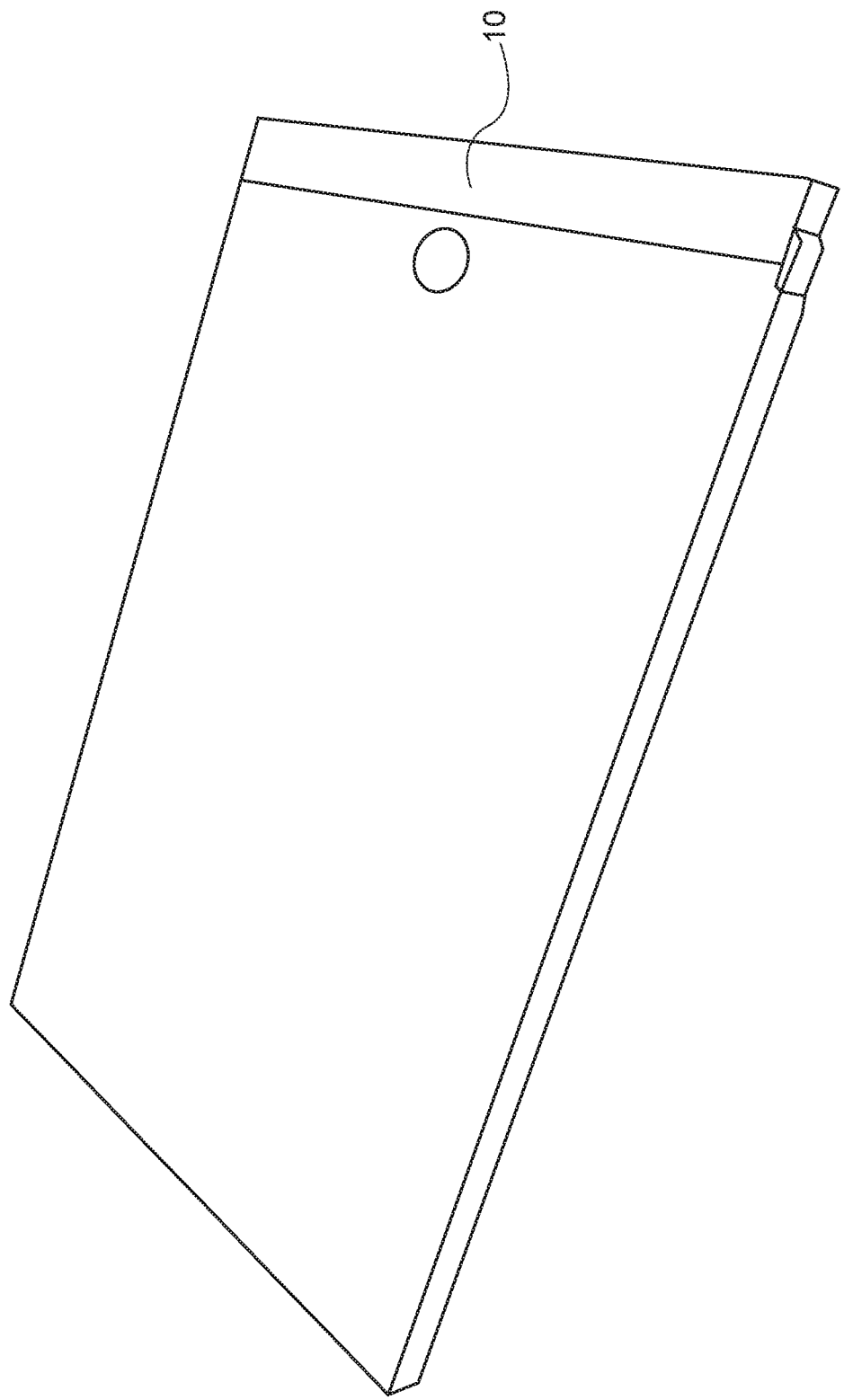
FIG. 2 shows a support container of the present invention.

Referring to FIG. 1, the biological materials in the bag are positioned in a support container (2). One exemplary support container (10) of this disclosure is depicted in FIG. 2. The support container (10) is adapted to receive the bag containing the biological material and to protect the bag from being punctured or otherwise damaged during freezing, such as in a walk in freezer, and transport. Two or more support containers are stackable horizontally or vertically. The support container also allows flattening of liquid filled bag to a thickness defined by the interior surface of the support container for more efficient storage and handling. The support container may be composed of metal or plastic or other suitable materials known in the art that will house and protect the bag of biological materials and withstand the transport and temperature extremes in the freezing process. The support container is preferably configured to receive the bag of biological material from the top thereof or the bottom thereof, as is evident in FIG. 3, which shows a bag of plasma (12) positioned in the support container (10) of FIG. 2.

Figure 3:
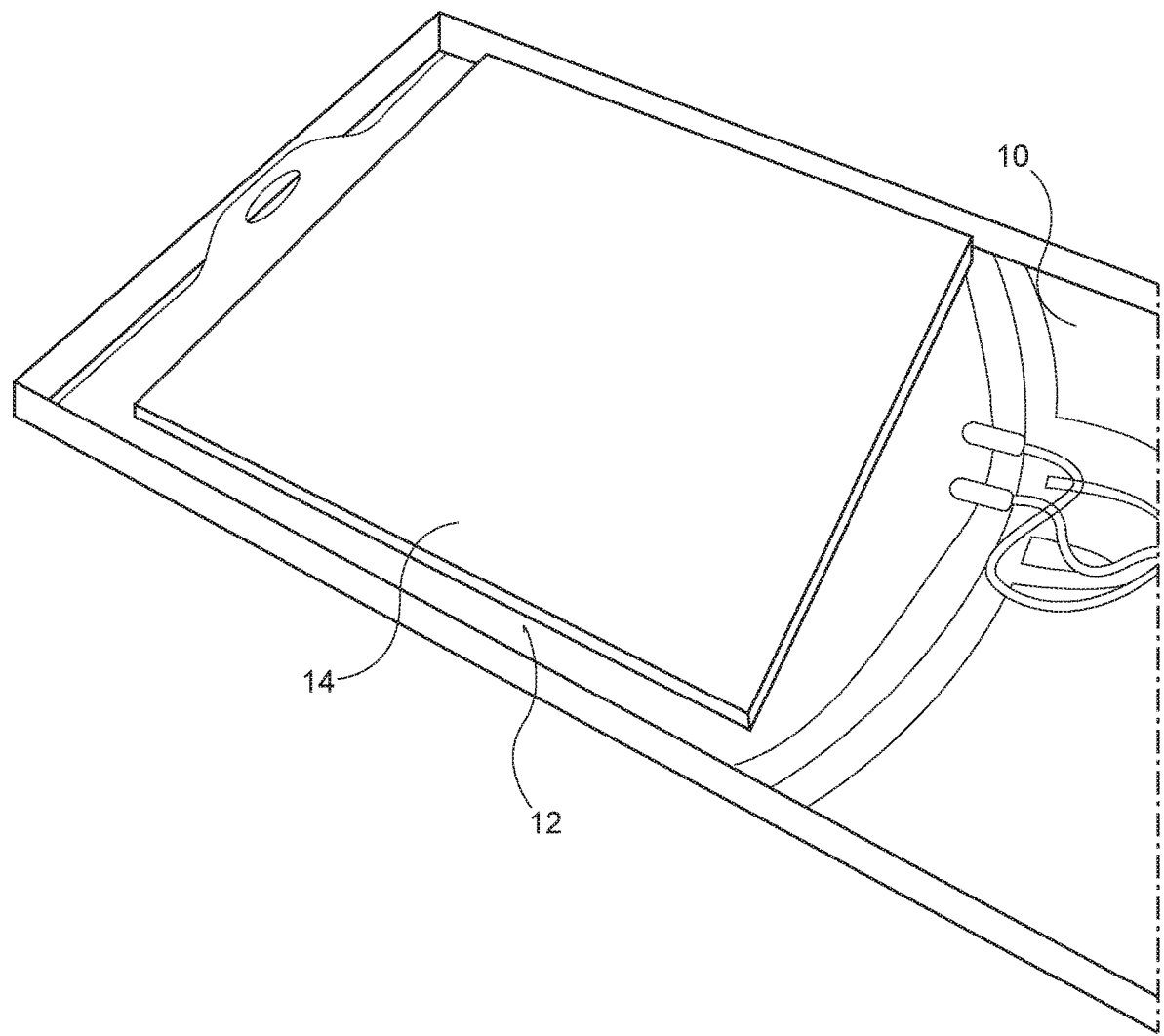
FIG. 3 shows a bag of biological material of the present invention disposed within a support container of the present invention under a compression pad of the present invention.

The bag of biological materials may be positioned within the support container with at least one compression pad (14), as depicted in FIG. 3. The at least one compression pad further restricts and compresses the bag within the support container to assure a uniform position and thickness of the bag during freezing within the support container. In this configuration, the bag of biological material is preferably of a size, and contains a volume of liquid biological material, such that the dimensions of the frozen bag of biological material retrieved from the support container has an internal height between about 0.127 cm (0.05 inches) and about 1.3 cm (0.5 inches). The dimensions of the support container may be approximately 22.9 cm×35.6 cm (9 inches×14 inches). The at least one compression pad may comprise a sheet of cross-linked polyethylene foam approximately 0.3 cm (0.125 inches) thick and having dimensions of about 33.7 cm×22 cm (13.25 inches×8.75 inches). The bag of biological material may be a 2 L bag or a 3 L bag that is filled with less than 500 mL of biological material, or less than 300 mL of biological material, or about 250 mL of biological material. Using bags of these dimensions and biological materials in these volumes results in the production and freezing of a bag of biological materials having an internal height that is between about 0.3 cm (0.10 inch) and about 1.3 cm (0.5 inch) and is herein referred to as an ultra-high surface area bag.

Referring to FIG. 1, a bag of biological materials positioned within the support container is frozen (3). The bag of biological materials may be compressed during the freezing process. As noted above, this may include the use of a support container that is sufficiently sturdy and is aligned to compress the bag of biological materials to achieve a frozen bag of biological material retrieved from the support container having an internal height between about 0.127 cm (0.05 inches) and about 1.3 cm (0.5 inches). This compression may also include the use of one or more compression pads positioned within the support container. The at least one compression pad further restricts and compresses the bag within the support container to assure a uniform position and thickness of the bag during freezing within the support container. In this configuration, the bag of biological material is preferably of a size, and contains a volume of liquid biological material, such that the dimensions of the frozen bag of biological material retrieved from the support container has an internal height between about 0.127 cm (0.05 inches) and about 1.3 cm (0.5 inches).

Compression of the bag of biological materials may include the application of weight to the outside of the support container during the freezing process such that the dimensions of the frozen bag of biological material retrieved from the support container has an internal height between about 0.127 cm (0.05 inches) and about 1.3 cm (0.5 inches). The weight may be in the form of external objects applied to the support container in order to compress the bag of biological materials and flatten and extend the frozen bag such that the dimensions of the frozen bag of biological material retrieved from the support container has an internal height between about 0.127 cm (0.05 inches) and about 1.3 cm (0.5 inches). The weight may also be in the form of one or more support containers stacked during the freezing process in order to apply pressure to the stack of support containers such that the dimensions of the frozen bag of biological material retrieved from the support container has an internal height between about 0.127 cm (0.05 inches) and about 1.3 cm (0.5 inches).

In similar embodiments, the bag of biological materials is compressed between two plates during the freezing process. The plates may be coupled by springs or the like to provide the correct tension and compression of the bag of biological materials in order to achieve a frozen bag of biological material retrieved from the support container having an internal height between about 0.127 cm (0.05 inches) and about 1.3 cm (0.5 inches).

In similar embodiments, the bag of biological materials may be compressed by hydraulic ram during the freezing process. The ram may be activated to provide compression to the bag of biological materials throughout the entire freezing process or during portions of the freezing process in order to achieve a frozen bag of biological material retrieved from the support container having an internal height between about 0.127 cm (0.05 inches) and about 1.3 cm (0.5 inches).

As noted above, the biological materials in the bag in the support container may be frozen at temperatures between 0° C. and −200° C., or colder. In order to freeze the biological materials in the bag, the support container is typically positioned in a freezer at the desired temperature for at least 12 hours and preferably for at least 18 hours and preferably for at least 24 hours. The bag of biological material in the support container is positioned horizontally in the freezer, and in this configuration, multiple support containers may be stacked horizontally in the freezer. Additional weight may be placed on top of the horizontally positioned support container(s). A small object of approximately 1 to 2 mL in volume are placed on top of the bag of biological materials when the bag is positioned in the support container before the support container is closed around the bag. In this configuration, the small object produces an indentation in the frozen bag of biological material which can be used to indicate which side of the bag of biological material was facing up when the bag of biological material was stored horizontally in the freezer and frozen. Additionally, this indentation in the frozen bag of biological materials may be used as an indicator of unintended thawing of the bag of biological material during transport or prior to the intended thawing of the bag of biological material at the time and location of the emergency use.

Referring to FIG. 1, frozen bags of biological material stored and protected in a support container may be transported to a patient in need of those biological materials prior to being rapidly thawed and administered to the patient. However, the bag of biological materials stored and frozen in a thin, flat, horizontal manner as described above, are fragile and must be carefully held in transport to maintain the frozen temperature of the biological material in the bag and to prevent the bag from breaking, leading to contamination and waste of the biological material, as well as contamination of the transport materials and/or vehicles with the spilled biological material. In order to do so safely, the frozen biological materials in the bag in the support container are introduced into a transport crate (4). The transport crate may be any container which can securely hold at least one support container and simultaneously maintain the temperature of the frozen biological materials within the support container(s). In one embodiment, a transport crate of the present invention comprises a metal exterior surrounding an insulating material, such as a high density polyethylene foam, expanded polystyrene (STYROFOAM™), pentane-blown polyurethane foam, aerogels, vacuum insulated panels, and the like. The insulating material comprises a void space of a specific size and dimension adapted to receive and secure at least one support container thereby further protecting the frozen biological material within the at least one support container and insulating the support container in order to maintain the biological material in the bag in a frozen state for transport from the original site of freezing of the biological material to a patient in need of such biological material. The transport crate may further include a lid configured to securely lock the at least one support container in the transport crate. The lid may further comprise insulating material to aid in securing the at least one support container in the transport crate and further aid in maintaining the present status of the biological material in the bag within the at least one support container.

Referring to FIG. 1, the frozen biological material and the support container within the transport crate may be housed in a vehicle for transport to the site of a patient in need of administration of the biological material (5). The vehicle may be an emergency response vehicle, such as an ambulance. As noted above, the frozen but fragile bag of biological material is protected and maintained in the support container deposed within the transport crate for transport to the site of the patient in need of such biological material. In this configuration, the frozen bag of biological material is protected and maintained in a frozen state until arrival at the site of the patient in need of such biological material.

Referring to FIG. 1, the bag of frozen biological material is removed from the transport crate and is then removed from the support container (6,7) in preparation of thawing the frozen biological material in the bag prior to the administration of the biological material to the patient.

Referring to FIG. 1, the frozen biological material is thawed (8) within the bag in a temperature control unit. The temperature control unit rapidly thaws and heats biological materials stored in the bag. The temperature control unit comprises at least one heating surface that comes into direct contact with the bag.

In one embodiment, the temperature control unit has at least two electrodes attached to at least two plates which are positioned to contact the sides of the bag of frozen biological materials and transfer heat from the plates to the bag of frozen biological materials, thereby thawing and heating the frozen biological materials. The thawing of frozen biological material in the bag may be facilitated by gentle mechanical agitation of the plates around the bag. The agitation may be vibrational agitation applied through the plates around the bag.

The temperature control unit may include a hollow bladder having flexible walls that come into contact with the bag of frozen material. A closed circulation system draws fluid from a closed reservoir and fills the bladder with a fluid heated to a specified temperature. The circulation system also drains fluid from the bladder. A heater in the reservoir heats the fluid before the fluid enters the bladder. As heated fluid flows through the bladder, heat is transferred through the bladder wall to the bag of biological materials to thaw the biological materials within the bag. The bladder wall expands against the bag as the bladder fills with fluid, and contracts from the plasma bag as the bladder is drained. The expansion and contraction of the bladder wall agitates the plasma bag and biological material to accelerate the thawing process. Suitable devices are disclosed in U.S. design Pat. No. D645,975 and U.S. Pat. No. 6,748,164, both of which are incorporated herein by reference in their entirety.

Unfortunately, for mobile transport of the frozen bags of biological material intended for rapid thawing, heating and administration to the patient in need thereof in a remote location under emergency conditions, the thawing devices of the prior art, including the US patent documents listed above, must be modified and improved to rapidly thaw such bags while remaining sufficiently stable and functional under rugged transport conditions associated with emergency vehicles.

For example, the fluid filled reservoir in the circulation system, as well as the components of the fluid connection with the flexible bladder must be closed and sealed to prevent the loss of fluid from the reservoir during transport. Additionally, the power source including sufficient power to run the circulation in the heating unit as well as a fan activated cooling system for the unit must be provided and adapted to run the rapid thawing device in an emergency vehicle.

In these embodiments, the temperature control unit is designed and programmed to thaw the biological materials within the bag in a closed hydraulic system that keeps the bag of biological materials dry, thereby maintaining the sterility of the bag during the following process, to prevent or minimize the growth of bacteria. A number of bladder configurations and circulation systems may be used within temperature control unit of the present invention. In a specific embodiment, the bladder has two cells in fluid connection with the circulation system. The circulation system is programmed to pressurize and depressurize the cells intermittently so that the cells expand and contract in different cycles to agitate the biological material within the bag and accelerate thawing.

The bladder is placed in direct contact with the bag of frozen biological materials to be thawed. In a specific embodiment, the bladder is configured to fold in half over and around the bag of frozen biological materials, which is placed between the two folds in the bladder such that the bladder covers the top and bottom of the bag. In this way, the bladder can agitate and transfer heat to both sides of the bag to efficiently thaw the frozen biological materials within the bag. In operation, a circulation system is configured to pump heated fluid in a continuous cycle from the reservoir to the bladder and withdraw fluid from the bladder back to the reservoir. The circulation system may include means to pump different amounts of heated fluid from the reservoir into the top and bottom portions of the bladder such that a portion of the bladder that resides on top of the bag of frozen biological material to be thawed receives a greater proportion of the heated fluid being pumped from the reservoir than is pumped into the bag residing beneath the bag of frozen biological materials to be thawed.

The temperature control unit is used to heat the frozen biological materials to various temperatures as may be required for different applications. Thus, the temperature for unit may be programmed to heat human plasma to a temperature of 37° C., which is compatible with human body temperature. Alternatively, the temperature control unit may be used to heat and maintain materials to temperatures above 37° C., including temperatures such as 50° C. or 60° C.

Thus, an aspect of this disclosure provides a method for thawing and heating biological materials in the bag. The bag is placed in contact with a hollow bladder having a flexible bladder wall. Fluid is heated to a desired temperature and pumped into the hollow bladder to expand the bladder wall against the bag and rapidly thaw and gently agitate the bag of frozen biological material. The heated fluid is maintained in the bladder to transfer heat through the bladder wall to the bag. Fluid is then withdrawn from the bladder to retract the bladder wall away from the bag.

The agitation of the bag of frozen biological material in these methods may include agitation provided by the water, and/or the walls, and/or the bladder in the temperature control unit. The agitation may be oscillating agitation, for example by waves in the water in the temperature control unit which flex the thawing bag of biological material. The agitation may be vibratory agitation, for example by applying vibration at approximately 60 Hertz to the bag, either directly or indirectly through the water, and/or the walls, and/or the bladder in the temperature control unit. Preferably, the agitation is progressive, such that the agitation of the rapidly thawing bag increases as the bag thaws. This further increases the thaw rate of the frozen bag of biological materials and also protects or prevents the tearing or rupture of the frozen bag that may be caused by agitation of the frozen bag soon after being placed in the temperature control unit. In this progressive agitation method, the agitation of the bag may increase, for example with vibrational agitation from as low as 5 Hertz to progressive increase to 60 Hertz or more.

Referring to FIG. 1, the thawed bag of biological materials is removed from the temperature control unit (9) and is ready for administration to a patient in need thereof.

Another aspect of the present invention provides a method for freezing, thawing, storing and preserving biological material(s). In these methods, a biological material is transferred to a bag of sufficient size and volume to form a bag of biological material having an interior height of less than 0.127 cm (0.05 inches). The biological material may be inserted into the bag through an opening into the interior of the bag, whereupon the conduit through which the biological material was inserted into the bag is closed. The closed bag of biological material(s) is then located in a support container configured to encapsulate and protect the bag of biological materials. The bag of biological materials is then frozen within the support container by locating the support container containing the frozen biological materials in a freezer for a time of at least 12 hours. Thereafter, the bag of frozen biological materials located within the support container may be retrieved from the freezer and transferred to a transport crate configured to receive, stabilize, and insulate the bag of frozen biological materials located within the support container. The transport crate holding the bag of frozen biological materials within the support container is then transported to the site of a patient in need of administration of the biological materials. The bag of frozen biological materials has been removed from the transport crate and removed from the support container. The bag of frozen biological material is then transferred to a temperature control unit in which the bag of frozen biological materials is thawed and heated to a desired temperature for administration of the thawed biological materials to a patient in need thereof. The bag of thawed and heated biological materials is then removed from the temperature control unit and the biological materials within the bag are administered to the patient in need thereof.

This disclosure further provides a system for conducting such methods comprising a bag of sufficient size and volume to form a bag of biological material having an interior height of less than 0.127 cm (0.05 inches), a support container configured to encapsulate and protect the bag of biological materials, a transport crate configured to receive, stabilize, and insulate the bag of biological materials located within the support container, a temperature control unit in which the bag of biological materials may be thawed and heated to a desired temperature.

Each publication or patent cited herein is incorporated herein by reference in its entirety.

The devices and methods disclosed herein are not to be limited in scope to the specific embodiments described herein. Indeed, various modifications of the devices and methods in addition to those described will become apparent to those of skill in the art from the foregoing description and accompanying figures. Such modifications are intended to fall within the scope of the appended claims.

What is claimed is:

1. A method for preparing a frozen bag of plasma material for rapid thawing at a site of a patient in need of urgent administration of the plasma material comprising:
   positioning a bag of plasma material in a support container configured to encapsulate and protect the bag of plasma material;
   positioning the support container in a freezer for a time of at least 12 hours in order to freeze the plasma material; and
   applying a compression force on the support container before the plasma material begins to freeze and during the time of freezing to compress the bag of plasma material to achieve a flat bag of frozen plasma material having a uniform thickness of less than or equal to 1.3 cm;
   wherein the compression force is an active external force supplied independent of the support container and is distributed uniformly across the bag to flatten the bag of plasma material.

2. The method of claim 1, wherein the uniform thickness is between about 0.127 cm and about 1.3 cm inclusive.

3. The method of claim 1, wherein the step of positioning the bag of plasma material within the support container in a freezer further comprises positioning the support container horizontally in the freezer, whereby the horizontal orientation of the support container and the compression force together result in the flat bag of frozen plasma material having the uniform thickness.

4. The method of claim 3, further comprising
   horizontally stacking two or more support containers; and
   applying the compression force simultaneously across the two or more support containers.

5. The method of claim 1, further comprising applying a weight to an external surface of the support container to provide the compression force on the bag of plasma material in the support container during freezing.

6. The method of claim 1, further comprising compressing the support container between two plates to provide the compression force on the bag of plasma material during freezing.

7. The method of claim 6, wherein the two plates are coupled by springs to provide the compression force sufficient to achieve the flat bag of frozen plasma material.

8. The method of claim 1, further comprising activating a hydraulic ram during at least a portion of the freezing process to provide the compression force on the support container during freezing.

9. The method of claim 1, wherein the compression force eliminates void spaces between the support container and the bag of plasma material to provide uniform flattening of the bag.

10. The method of claim 1, wherein the uniform thickness of the bag of frozen plasma material is such that the bag of frozen plasma material can completely thaw to 37° C. in three minutes or less in a standard temperature control unit.

11. A method of forming a frozen bag of plasma material having a size and shape suitable for rapid thawing in a standard temperature control unit located at a site of a patient in need of immediate administration of the thawed plasma material, the method comprising:
   placing a bag of plasma material in a support container, wherein the bag of plasma material flattens to a thickness defined by an interior surface of the support container;
   placing the support container in a freezer for an amount of time selected to freeze all of the plasma material; and
   compressing the bag of plasma material with an active external force before the plasma material begins to freeze and during the amount of time of freezing to further flatten the bag of plasma material such that the plasma material when frozen has a uniform thickness and a large surface area to volume ratio that allows the frozen plasma material to rapidly thaw in less than 20 minutes when the bag of frozen plasma material is placed in the standard temperature control unit;
   wherein the active external force is supplied independent of the support container and is distributed uniformly across the bag to flatten the bag of plasma material.

12. The method of claim 11, wherein the plasma material fills less than 25% of the volume of the bag such that when the bag of plasma material is compressed during freezing the plasma material flattens within the bag to a thickness less than or equal to 1.3 cm.

13. The method of claim 11, further comprising inserting one or more compression pads within the support container adjacent to the bag of plasma material to maintain uniform thickness of the bag of plasma material in the support container during freezing.

14. The method of claim 13, wherein the one or more compression pads are comprised of a sheet of cross-linked polyethylene foam.

15. The method of claim 11, further comprising draining gas from the bag before freezing.

16. The method of claim 11, wherein the thickness of the frozen plasma material allows the frozen plasma material to completely thaw to 37° C. in three minutes or less in the standard temperature control unit.

17. The method of claim 11, wherein the uniform thickness is between 0.127 cm and 1.3 cm, inclusive.

18. A method of shaping a bag of frozen plasma material to facilitate rapid thawing of the frozen plasma material for use in an emergency situation, the method comprising:

placing a support container having a bag of plasma material stored therein in a freezer, wherein the bag of plasma material is protected from damage during freezing by the support container; and exerting a compressive force on the bag of plasma material before the plasma material begins to freeze and during freezing to create a bag of frozen plasma material having a flat shape and uniform thickness, wherein the frozen plasma material is configured to thaw in less than 20 minutes when the bag is placed in a standard temperature control unit, and the compressive force is an active external force supplied independent of the support container and is distributed uniformly across the bag to flatten the bag of plasma material.

19. The method of claim 18, wherein the flat shape and uniform thickness result in the frozen plasma material completely thawing to 37° C. in three minutes or less in the standard temperature control unit for rapid use of the plasma material in the emergency situation.

20. The method of claim 18, where the bag having the frozen plasma material stored therein has an ultra-high surface area that allows the plasma material to form the flat shape with the uniform thickness when the bag of plasma material is compressed.

* * * * *